United States Patent
Zhang et al.

(10) Patent No.: US 11,701,349 B2
(45) Date of Patent: *Jul. 18, 2023

(54) PHARMACEUTICAL COMPOSITION CONTAINING QUINOLINE DERIVATIVE

(71) Applicant: JIANGSU HENGRUI MEDICINE CO., LTD., Jiangsu (CN)

(72) Inventors: Xinhua Zhang, Lianyungang (CN); Chenyang Wang, Lianyungang (CN); Daimei Zhang, Lianyungang (CN); Jianfeng Bai, Lianyungang (CN)

(73) Assignee: JIANGSU HENGRUI MEDICINE CO., LTD., Jiangsu (CN)

( * ) Notice: Subject to any disclaimer, the term of this patent is extended or adjusted under 35 U.S.C. 154(b) by 246 days.

This patent is subject to a terminal disclaimer.

(21) Appl. No.: 16/757,363

(22) PCT Filed: Oct. 23, 2018

(86) PCT No.: PCT/CN2018/111388
§ 371 (c)(1),
(2) Date: Apr. 17, 2020

(87) PCT Pub. No.: WO2019/080830
PCT Pub. Date: May 2, 2019

(65) Prior Publication Data
US 2021/0186952 A1   Jun. 24, 2021

(30) Foreign Application Priority Data
Oct. 24, 2017 (CN) .......................... 201711002771.4

(51) Int. Cl.
A61K 31/4709 (2006.01)
A61K 9/20 (2006.01)
A61K 9/48 (2006.01)

(52) U.S. Cl.
CPC ........ *A61K 31/4709* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 9/4833* (2013.01); *A61K 9/4858* (2013.01); *A61K 9/4866* (2013.01)

(58) Field of Classification Search
CPC .. A61K 9/2013; A61K 9/2018; A61K 9/2027; A61K 9/2054; A61K 9/2095; A61K 9/4833; A61K 9/4858; A61K 9/4866; A61K 31/4709; A61P 35/00; A61P 35/04
See application file for complete search history.

(56) References Cited

U.S. PATENT DOCUMENTS

| | | |
|---|---|---|
| 8,790,708 B2 | 7/2014 | Ashraf et al. |
| 8,901,140 B2 | 12/2014 | Tang et al. |
| 9,309,226 B2 | 4/2016 | Sun et al. |
| 2013/0338190 A1 | 12/2013 | Li et al. |
| 2019/0054025 A1 | 2/2019 | Lu et al. |
| 2020/0138803 A1 | 5/2020 | Lu et al. |

FOREIGN PATENT DOCUMENTS

| | | | |
|---|---|---|---|
| CN | 102471312 B | * | 6/2014 |
| CN | 102933574 B | | 10/2014 |
| CN | 103974949 B | | 11/2015 |
| CN | 106913529 A | | 7/2017 |
| WO | 2017129087 A1 | | 8/2017 |
| WO | 2017129088 A1 | | 8/2017 |

OTHER PUBLICATIONS

International Search Report issued in International Patent Application No. PCT/CN2018/111388 dated Jan. 17, 2019, with English translation, 5 pages.
English translation of Written Opinion of the International Searching Authority issued in International Patent Application No. PCT/CN2018/111388 dated Jan. 17, 2019, 3 pages.
Taiwan Office Action issued in Chinese Patent Application No. 107137346 dated Sep. 26, 2019, with English translation, 9 pages.
Huang, Anni, "No more random mixing," Scientific Development, Issue 513, Sep. 2015 (6 pages).
Shao, L. et al., Lactobacillus plantarum strain BDLP000116S ribosomal RNA gene, partial sequence, Gen Bank Register No. JN786879. 1, Online, Nov. 7, 2011 (2 pages).
Chinese Patent Application No. 201711002771.4 filed Oct. 24, 2017 (not published).

\* cited by examiner

*Primary Examiner* — David Browe
(74) *Attorney, Agent, or Firm* — Foley & Lardner LLP

(57) ABSTRACT

The present invention provides a pharmaceutical composition comprising (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide or a pharmacologically acceptable salt thereof, which is obtained by mixing the quinoline derivative or a pharmacologically acceptable salt thereof, a wetting agent, a disintegrant, and at least one pharmaceutical excipient; granulating; dynamic drying; and optionally compressing into tablets or filling into capsules after mixing with a lubricant.

17 Claims, 5 Drawing Sheets

PHARMACEUTICAL COMPOSITION CONTAINING QUINOLINE DERIVATIVE

BACKGROUND OF THE INVENTION

Field of the Invention

The invention relates to the field of pharmaceutical preparations and, specifically, relates to a process for preparing a pharmaceutical composition comprising (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide or a pharmacologically acceptable salt thereof.

Description of Related Art

Protein kinases (PKs) can be divided into two categories: protein tyrosine kinases and serine-threonine kinases. PTKs can phosphorylate tyrosine residues on proteins, and STKs can phosphorylate serine and threonine residues. Tyrosine kinase can be divided into receptor type and non-receptor type. At present, 90 types of tyrosine kinase-encoding genes have been identified in human genes, of which about 60 types belong to receptor type and about 30 types belong to non-receptor type.

CN102471312B disclosed a small molecule receptor tyrosine kinase inhibitor (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide, the compound has a structure represented by Formula I,

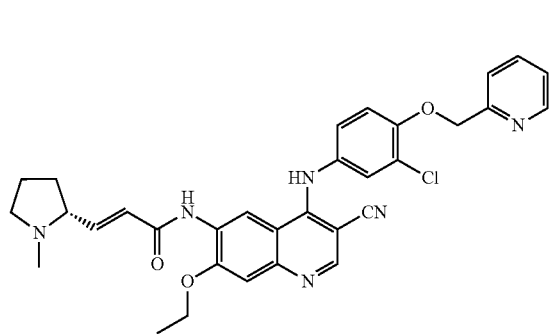

I

CN102933574B disclosed a maleate form of the compound of Formula I, which has advantages over other salts and the compound of Formula I itself in terms of solubility, bioavailability and pharmacokinetics.

CN103974949B disclosed type I crystal form of a dimaleate salt of the compound of Formula I. The crystal form has good crystal form stability and chemical stability, and can be used for preparing a medicine for treating diseases related to EGFR receptor tyrosine kinase or HER-2 receptor tyrosine kinase.

WO2017129087 and WO2017129088 disclosed a pharmaceutical composition comprising (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide or a pharmacologically acceptable salt thereof. The process for preparing comprises the steps of mixing the active ingredient with pharmaceutically acceptable excipients, wet granulating, drying, and compressing into tablets or filling into capsules. The pharmaceutical composition dissolves rapidly and the dissolution rate of samples is uniform among batches. However, when the process of WO2017129087 or WO2017129088 was scaled up, the dissolution rate of the obtained samples was significantly lower than that of the samples from the corresponding pilot test batch, and the dissolution rate of the pharmaceutical preparation was not uniform among batches. The factors that affect the dissolution rate of the pharmaceutical composition are complex. Any one or more of the factors such as the types, proportions and moisture of the pharmaceutical excipients in the prescription, particle size, tableting speed and hardness may affect the final dissolution rate. Therefore, it is very difficult to provide a pharmaceutical composition that maintains the required dissolution rate and maintains uniformity among batches after being scaled up.

In the field of pharmaceutical preparations, there are many ways to dry samples, such as drying under atmospheric pressure, drying under reduced pressure, spray drying, fluidized drying, freeze drying, infrared drying, microwave drying, moisture absorption drying. Each drying method has its own advantages and disadvantages. When choosing a drying method, technicians usually choose the simple and easy one with low energy consumption, such as drying under reduced pressure. In the pilot test stage of the formulation research, drying under reduced pressure or blast drying under atmospheric pressure is more preferred.

The invention unexpectedly discovered that by adopting dynamic drying for the process of drying after granulating, the dissolution rate of the obtained pharmaceutical composition can reach the level of the samples from the pilot test batch, and the dissolution rate is uniform among batches.

BRIEF SUMMARY OF THE INVENTION

The present invention provides a pharmaceutical composition comprising an active ingredient (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide or a pharmacologically acceptable salt thereof. The pharmaceutical composition is obtained by mixing the active ingredient, a wetting agent with at least one pharmaceutical excipient optionally selected from a disintegrant, a filler, an adhesive or a lubricant, granulating, dynamic drying, and optionally compressing into tablets or filling into capsules after mixing with a lubricant.

Based on the total weight of the pharmaceutical composition, the content of the active ingredient is 5-70%, preferably 10-50%. In an embodiment, it can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50%, and more preferably 20-40%.

Further, the wetting agent of the present invention is selected from but not limited to at least one of ethanol, methanol, acetone, isopropanol and water, preferably at least one of ethanol, methanol and water, and more preferably ethanol/water. In some embodiments, the content of ethanol in ethanol/water may be 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, preferably 50-95%, and more preferably 80-95%.

In some embodiments, dynamic drying is drying the material in motion by mechanical stirring in the drying container or introducing a dry air flow into the drying container. Both drying while stirring and fluidized drying belong to this drying method. The dynamic drying in the present invention is selected from but not limited to stirring drying and fluidized drying, and preferably fluidized drying.

In other embodiments, the granulating method of the present invention adopts a high-speed shear granulating method or a fluidized bed spray granulating method.

The high-speed shear granulating method of the present invention refers to adding the components to be granulated into a high-speed shear wet granulator, and adding the adhesive liquid into the granulator under the dynamic conditions of stirring and mixing and high-speed shear for wet granulating.

The fluidized bed spray granulating method of the present invention refers to adding the components to be granulated into a fluidized bed, introducing gas into the fluidized bed to make the material in a fluidized state and spraying the adhesive liquid into the fluidized bed for granulating.

The disintegrant of the present invention is selected from the group consisting of low-substituted hydroxypropyl cellulose, cross-linked sodium carboxymethyl cellulose, sodium carboxymethyl starch and cross-linked polyvinyl pyrrolidone. The content of the disintegrant is preferably 2-20% based on the total weight of the composition.

The filler of the present invention is selected from the group consisting of microcrystalline cellulose, calcium hydrogen phosphate, mannitol, pregelatinized starch and lactose. Based on the total weight of the composition, the content of the filler is about 5-80%, which may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80%.

The adhesive of the present invention is preferably selected from the group consisting of hydroxypropyl methylcellulose, hydroxypropyl cellulose, sodium carboxymethyl cellulose, polyvinylpyrrolidone and methyl cellulose. Based on the total weight of the composition, the content of the adhesive is about 0.5-15%, which can be 0.5, 0.6, 0.7, 0.8, 0.9, 1, 2, 3, 4, 5, 6, 7, 8, 9, 10, 11, 12, 13, 14, 15%.

The lubricant of the present invention is selected from the group consisting of talc, magnesium stearate, zinc stearate, glyceryl behenate, sodium lauryl sulfate, hydrogenated vegetable oil and colloidal silica. Based on the total weight of the composition, the content of the lubricant is about 0.5-5%, which may be 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0%.

The pharmacologically acceptable salt of (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide of the present invention may be selected from but not limited to hydrochloride, maleate, hydrobromide, p-toluenesulfonate, mesylate, sulfate or ethanesulfonate, preferably maleate, more preferably dimaleate.

In a preferred embodiment, the pharmaceutical composition of the present invention comprises:
1) 2-20 wt % of a disintegrant, the disintegrant is cross-linked polyvinyl pyrrolidone;
2) 5-80 wt % of a filler, the filler is selected from at least one of lactose and microcrystalline cellulose;
3) 0.5-15 wt % of an adhesive, the adhesive is selected from at least one of polyvinylpyrrolidone, hydroxypropyl methylcellulose and hydroxypropyl cellulose;
4) 0.5-5 wt % of a lubricant, the lubricant is selected from at least one of magnesium stearate and talc.

In some embodiments, when the batch feeding is in the kilogram grade (for example, 1 kg), the above-mentioned pharmaceutical composition is under the condition of a 0.1 mol/L hydrochloric acid solution medium, the dissolution rate (%) of the active ingredient in the pharmaceutical composition can still reach 85% or higher at 30 minutes, preferably 90% or higher. Further, the dissolution rate (%) of the active ingredient in the pharmaceutical composition reaches 50% or higher at 15 minutes, and may be greater than or equal to 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95%. The solid preparation dissolves quickly and completely, has good bioavailability, and its preparing process is simple, and is suitable for scale-up production.

The present invention also provides a process for preparing the aforementioned pharmaceutical composition, comprising:
a) mixing the active ingredient (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide or a pharmacologically acceptable salt thereof with at least one pharmaceutical excipient optionally selected from a disintegrant, a filler, an adhesive or a lubricant;
b) adding a wetting agent for wet granulating;
c) dynamic drying, which is preferably fluidized drying;
d) adding lubricant, and compressing into tablets after mixing.

The parameters set for fluidized drying of the present invention are as follows: fan flow of 5-15 m$^3$/min, inlet air temperature of 50-70° C., material temperature of 20-55° C., drying time of 10-30 min.

The pharmaceutical composition obtained by the process for preparing provided by the present invention dissolves rapidly and has significant effects, and can be used for the treatment of gastric cancer, lung cancer or breast cancer.

The pharmaceutical excipients or reagents described in the present invention can be obtained from commercial sources. Compound A: (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide or a pharmacologically acceptable salt thereof can be prepared by referring to the method described in CN102471312B.

BRIEF DESCRIPTION OF THE SEVERAL VIEWS OF THE DRAWING(S)

DETAILED DESCRIPTION OF THE INVENTION

The present invention is further illustrated by the following examples and experimental examples. These examples and experimental examples are for illustrative purposes only and are not intended to limit the scope of the invention.

Examples 1-5

(R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide maleate (hereinafter referred as Compound A), lactose, microcrystalline cellulose, polyvinylpyrrolidone and cross-linked polyvinylpyrrolidone were mixed according to the prescription ratio prescription in Table 1, wet granulation was carried out by using an appropriate amount of 20 wt % aqueous ethanol, anhydrous ethanol, and 93.75 wt % aqueous ethanol as wetting agents. The wet particles were placed in a fluidized bed, and the fan flow was set at 5-15 m³/min, inlet air temperature was set at 50-70° C., material temperature was set at 20-55° C., and drying time was set at 10-30 min. Dynamic drying was performed until the moisture became less than 2%, and dry granulating was carried out, the prescription amount of magnesium stearate was added, and mixed in a rotary mixer. The obtained total mixed particles were compressed and coated to prepare tablets.

TABLE 1

| Ingredient | Example 1 | Example 2 | Example 3 | Example 4 | Example 5 |
|---|---|---|---|---|---|
| Preparation quantity (kg) | 10.3 | 7.3 | 9.0 | 18.0 | 6.4 |
| Compound A | 27.1 | 38.1 | 31.1 | 15.5 | 43.6 |
| Lactose | 40.6 | 29.6 | 36.6 | 52.2 | 24.1 |
| Microcrystaline cellulose | 20.0 | 20.0 | 20.0 | 20.0 | 20.0 |
| Cross-linked polyvinylpyrrolidone | 8 | 8 | 8 | 8 | 8 |
| Polyvinylpyrrolidone | 3.3 | 3.3 | 3.3 | 3.3 | 3.3 |
| Magnesium stearate | 1.0 | 1.0 | 1.0 | 1.0 | 1.0 |
| Total | 100 | 100 | 100 | 100 | 100 |
| Wetting agent | 20 wt % aqueous ethanol | anhydrous ethanol | 93.75 wt % aqueous ethanol | 93.75 wt % aqueous ethanol | 93.75 wt % aqueous ethanol |

Unit: mass %.

Experimental Example 1: Dissolution Experiment

Figure 1:
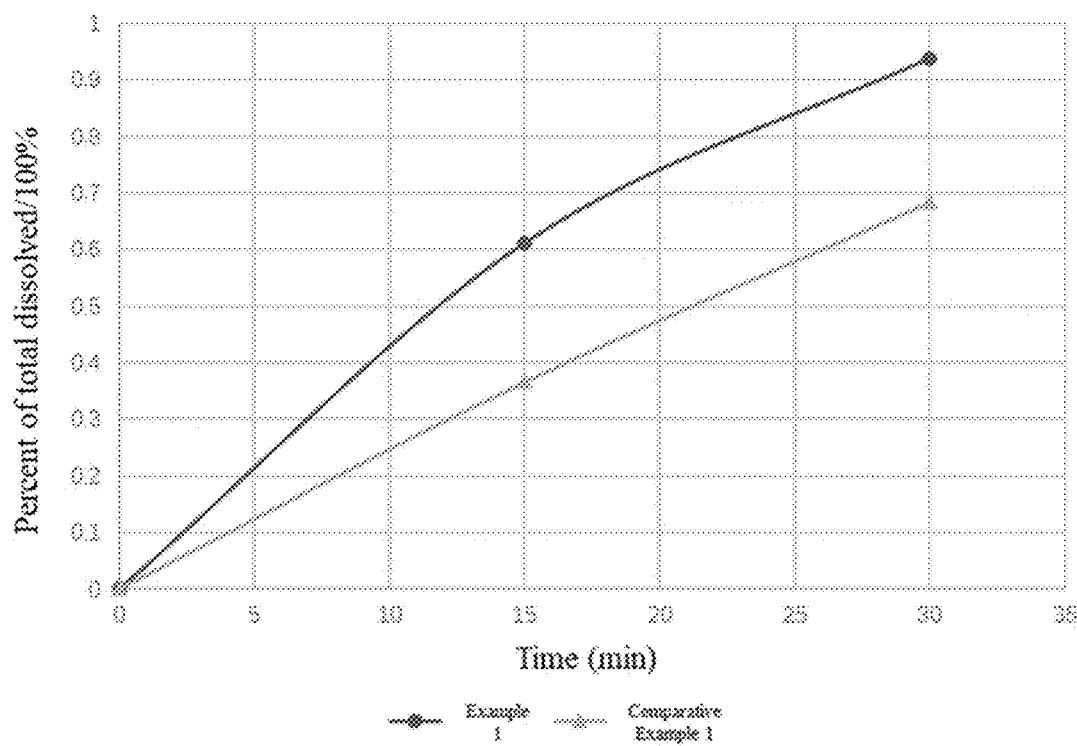
FIG. 1 shows the dissolution curves of tablets of Example 1 and Comparative Example 1 in 0.1 mol/L of hydrochloric acid solution
Figure 2:
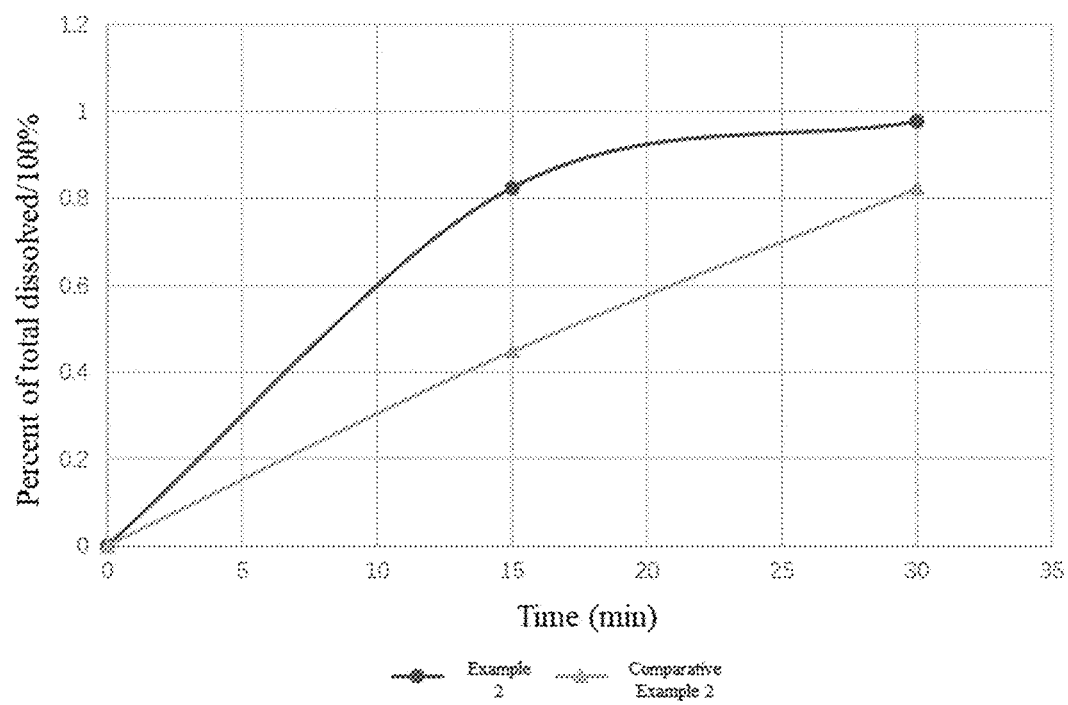
FIG. 2 shows the dissolution curves of tablets of Example 2 and Comparative Example 2 in 0.1 mol/L of hydrochloric acid solution.
Figure 3:
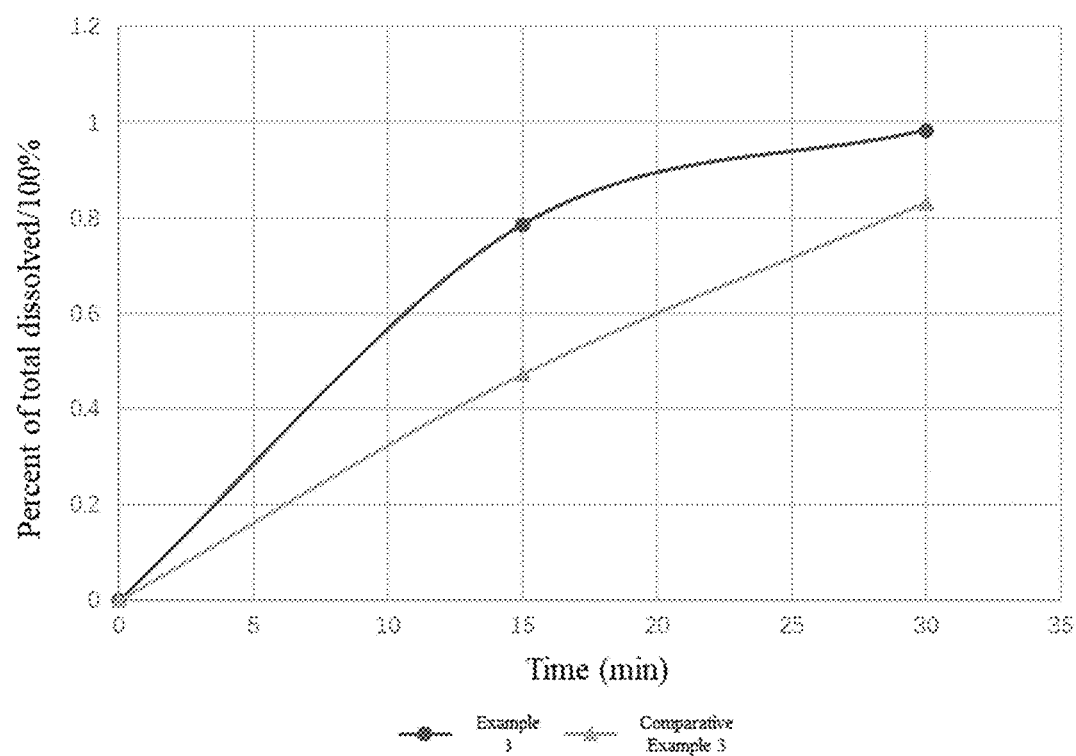
FIG. 3 shows the dissolution curves of tablets of Example 3 and Comparative Example 3 in 0.1 mol/L of hydrochloric acid solution.
Figure 4:
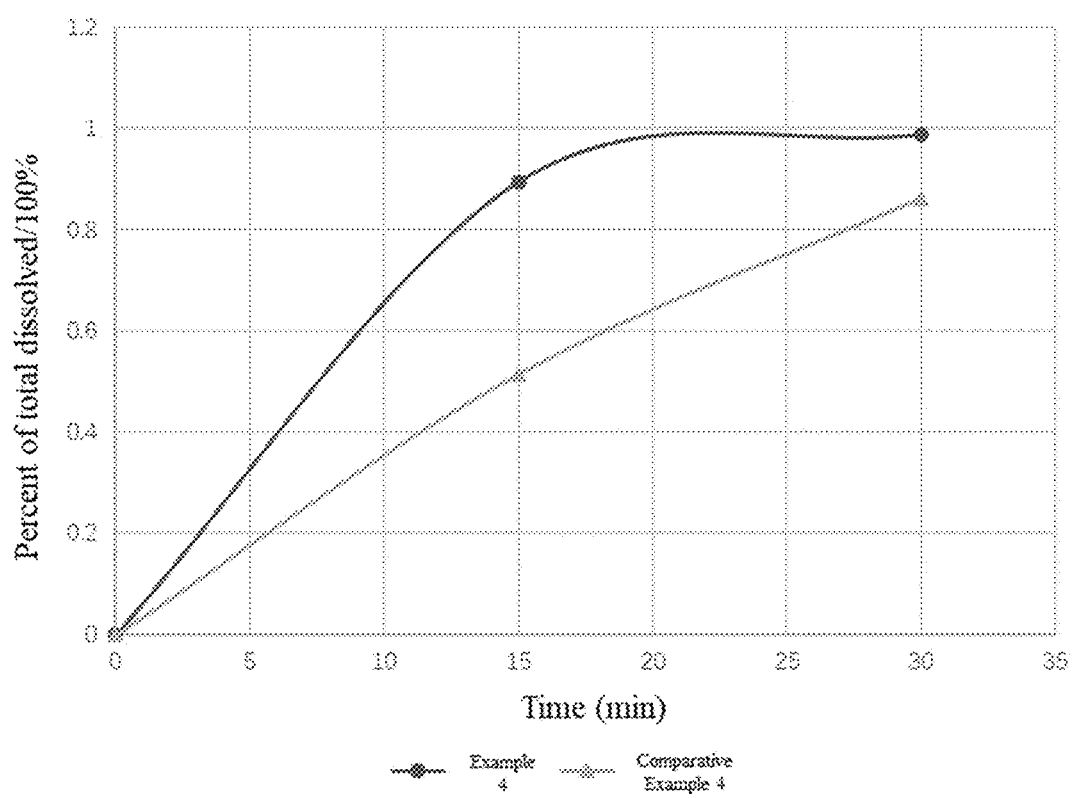
FIG. 4 shows the dissolution curve of tablets of Example 4 and Comparative Example 4 in 0.1 mol/L of hydrochloric acid solution.
Figure 5:
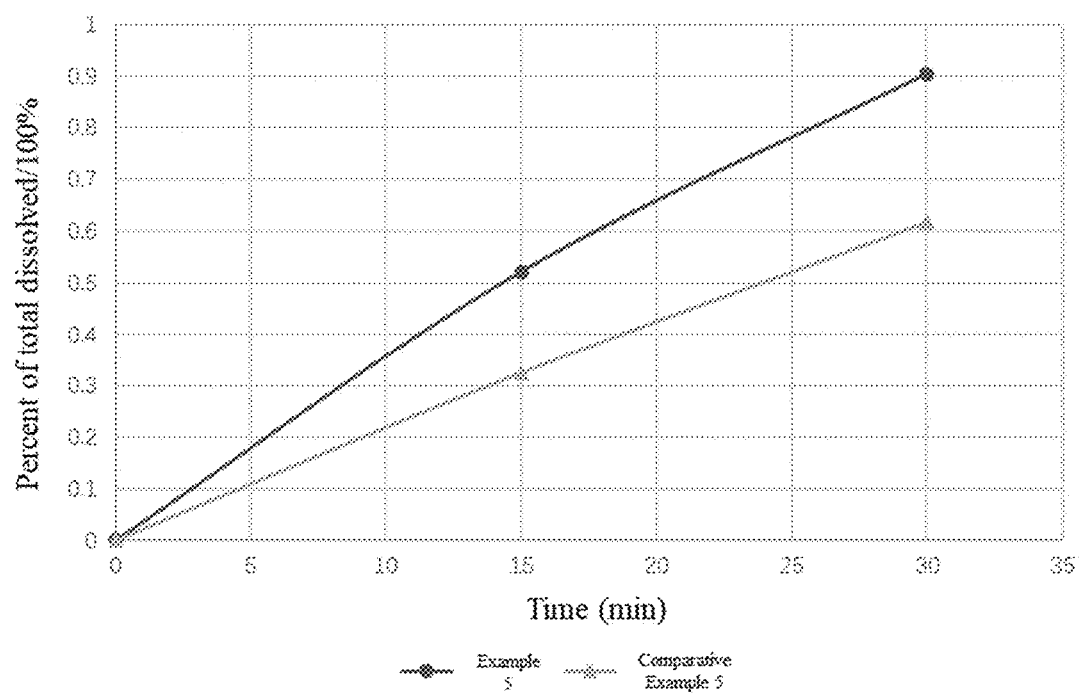
FIG. 5 shows the dissolution curve of tablets of Example 5 and Comparative Example 5 in 0.1 mol/L of hydrochloric acid solution.

The dissolution rates of tablets of Examples 1-5 were measured according to the second method of General Regulation 0931 of the Chinese Pharmacopoeia 2015 (Volume IV). 900 mL of a 0.1 mol/L hydrochloric acid solution was used as the dissolution medium, and a dissolution test was performed at a paddle speed of 50 rpm at 37±0.5° C. The results show that Compound A in the particles prepared by the dynamic drying process in Examples 1-5 was dissolved rapidly and completely. The results of the dissolution experiment are shown in Table 2 and the comparison diagrams of the dissolution curves are shown in FIGS. 1-5.

TABLE 2

| Time | Dissolution rates (%) | | | | |
|---|---|---|---|---|---|
| (min) | Example 1 | Example 2 | Example 3 | Example 4 | Example 5 |
| 15 | 61.2 | 82.5 | 78.6 | 89.5 | 52.2 |
| 30 | 93.9 | 97.7 | 98.4 | 98.8 | 90.5 |

Comparative Examples 1-5

(R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide maleate (hereinafter referred as Compound A), lactose, microcrystalline cellulose, polyvinylpyrrolidone and cross-linked polyvinylpyrrolidone were mixed according to the prescription ratio in Table 3, wet granulation was carried out by using an appropriate amount of 20 wt % a aqueous ethanol, anhydrous ethanol, and 93.75 wt % aqueous ethanol as wetting agents. The wet particles were placed in a blast air drying oven, and dried at the drying temperature set at 50-60° C. for 60-180 min, the particles were turned over every 30 min. Static drying was performed until the moisture became less than 2%, and dry granulating was carried out, the prescription amount of magnesium stearate was added, and mixed in a rotary mixer. The obtained total mixed particles were compressed and coated to prepare tablets.

TABLE 3

| Ingredient | Comparative Example 1 | Comparative Example 2 | Comparative Example 3 | Comparative Example 4 | Comparative Example 5 |
|---|---|---|---|---|---|
| Preparation quantity (kg) | 10.3 | 7.3 | 9.0 | 18.0 | 6.4 |
| Compound A | 27.1 | 38.1 | 31.1 | 15.5 | 43.6 |
| Lactose | 40.6 | 29.6 | 36.6 | 52.2 | 24.1 |
| Microcrystaline cellulose | 20.0 | 20.0 | 20.0 | 20.0 | 20.0 |
| Cross-linked polyvinylpyrrolidone | 8 | 8 | 8 | 8 | 8 |
| Polyvinylpyrrolidone | 3.3 | 3.3 | 3.3 | 3.3 | 3.3 |
| Magnesium stearate | 1.0 | 1.0 | 1.0 | 1.0 | 1.0 |
| Total | 100 | 100 | 100 | 100 | 100 |
| Wetting agent | 20 wt % aqueous ethanol | anhydrous ethanol | 93.75 wt % aqueous ethanol | 93.75 wt % aqueous ethanol | 93.75 wt % aqueous ethanol |

Unit: mass %.

Experimental Example 2: Dissolution Experiment

The dissolution rates of tablets of Comparative Examples 1-5 were measured according to the second method of General Regulation 0931 of the Chinese Pharmacopoeia 2015 (Volume IV). 900 mL of a 0.1 mol/L hydrochloric acid solution was used as the dissolution medium, and a dissolution test was performed at a paddle speed of 50 rpm at 37±0.5° C. The results show that the dissolution rate of the Compound A in the tablets of Comparative Examples 1-5 prepared by the static drying process was significantly lower than that of the tablets with the same prescription of Examples prepared by the dynamic drying process. The results of the dissolution experiments are shown in Table 4, and the comparison diagrams of the dissolution curves are shown in FIGS. 1-5.

TABLE 4

| | Dissolution rates (%) | | | | |
|---|---|---|---|---|---|
| Time (min) | Comparative Example 1 | Comparative Example 2 | Comparative Example 3 | Comparative Example 4 | Comparative Example 5 |
| 15 | 36.6 | 44.8 | 47.2 | 51.4 | 32.5 |
| 30 | 68.4 | 82.3 | 83.1 | 86.3 | 61.7 |

What is claimed is:

1. A pharmaceutical composition comprising an active ingredient (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide or a pharmacologically acceptable salt thereof, a disintegrant, a filler, an adhesive and a lubricant;
   the pharmaceutical composition is obtained by a) mixing the active ingredient (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide or the pharmacologically acceptable salt thereof with the disintegrant, the filler, and the adhesive;
   b) wet granulating by adding a wetting agent;
   c) fluidized drying;
   d) adding the lubricant and mixing; and
   e) compressing into tablets or filling into capsules;
      wherein the wetting agent is ethanol or ethanol and water, wherein the disintegrant is cross-linked polyvinyl pyrrolidone, and wherein the wet granulating is fluidized bed spray granulating.

2. The pharmaceutical composition according to claim 1, wherein the filler is selected from the group consisting of microcrystalline cellulose, calcium hydrogen phosphate, mannitol, pregelatinized starch, and lactose.

3. The pharmaceutical composition according to claim 1, wherein the adhesive is selected from the group consisting of hydroxypropyl methylcellulose, hydroxypropyl cellulose, sodium carboxymethyl cellulose, polyvinylpyrrolidone, and methyl cellulose.

4. The pharmaceutical composition according to claim 1, wherein the lubricant is selected from the group consisting of talc, magnesium stearate, zinc stearate, glyceryl behenate, sodium lauryl sulfate, hydrogenated vegetable oil, and colloidal silica.

5. The pharmaceutical composition according to claim 1, wherein the filler is selected from the group consisting of microcrystalline cellulose, calcium hydrogen phosphate, mannitol, pregelatinized starch, and lactose;
   the adhesive is selected from the group consisting of hydroxypropyl methylcellulose, hydroxypropyl cellulose, sodium carboxymethyl cellulose, polyvinylpyrrolidone, and methyl cellulose; and
   the lubricant is selected from the group consisting of talc, magnesium stearate, zinc stearate, glyceryl behenate, sodium lauryl sulfate, hydrogenated vegetable oil, and colloidal silica.

6. The pharmaceutical composition according to claim 1, wherein the pharmacologically acceptable salt is maleate.

7. The pharmaceutical composition according to claim 1, wherein the content of the active ingredient is 5%-70%, based on the total weight of the composition.

8. The pharmaceutical composition according to claim 1, wherein the content of the disintegrant is 2-20% based on the total weight of the composition.

9. The pharmaceutical composition according to claim 2, wherein the content of the filler is 5-80% based on the total weight of the composition.

10. The pharmaceutical composition according to claim 3, wherein the content of the adhesive is 0.5-15% based on the total weight of the composition.

11. The pharmaceutical composition according to claim 4, wherein the content of the lubricant is 0.5-5% based on the total weight of the composition.

12. The pharmaceutical composition according to claim 1, wherein the pharmaceutical composition comprises:
   1) 2-20 wt % of disintegrant, the disintegrant is cross-linked polyvinyl pyrrolidone;
   2) 5-80 wt % of filler, the filler is selected from at least one of lactose and microcrystalline cellulose;
   3) 0.5-15 wt % of adhesive, the adhesive is selected from at least one of polyvinylpyrrolidone, hydroxypropyl methylcellulose and hydroxypropyl cellulose; and
   4) 0.5-5 wt % of a lubricant, the lubricant is selected from at least one of magnesium stearate and talc.

13. The pharmaceutical composition according to claim 1, wherein the dissolution rate (%) of the active ingredient in the pharmaceutical composition reaches 85% or higher at 30 minutes in a 0.1 mol/L hydrochloric acid solution.

14. A process for preparing the pharmaceutical composition according to claim 1, comprising:
   a) mixing the active ingredient (R, E)-N-(4-(3-chloro-4-(pyridin-2-ylmethoxy) phenylamino)-3-cyano-7-ethoxyquinolin-6-yl)-3-(1-methylpyrrolidinyl-2-yl)-acrylamide or the pharmacologically acceptable salt thereof with the disintegrant, the filler, and the adhesive;
   b) wet granulating by adding the wetting agent;
   c) fluidized drying; and
   d) adding the lubricant and mixing; and
   e) compressing into tablets or filling into capsules.

15. The process for preparing the pharmaceutical composition according to claim 14, wherein the filler is selected from the group consisting of microcrystalline cellulose, calcium hydrogen phosphate, mannitol, pregelatinized starch, and lactose;
   the adhesive is selected from the group consisting of hydroxypropyl methylcellulose, hydroxypropyl cellulose, sodium carboxymethyl cellulose, polyvinylpyrrolidone, and methyl cellulose; and
   the lubricant is selected from the group consisting of talc, magnesium stearate, zinc stearate, glyceryl behenate, sodium lauryl sulfate, hydrogenated vegetable oil, and colloidal silica.

16. A method for treating cancer comprising administering to a subject thereof a therapeutically effective amount of the pharmaceutical composition according to claim 1.

17. The method of claim 16, wherein the cancer is gastric cancer, lung cancer or breast cancer.

\* \* \* \* \*